(12) United States Patent
Podgornik et al.

(10) Patent No.: US 6,736,973 B1
(45) Date of Patent: May 18, 2004

(54) CHROMATOGRAPHIC DEVICE

(75) Inventors: Ales Podgornik, Ljubljana (SI); Milos Barut, Ljubljana (SI); Ales Strancar, Ljubljana (SI); Djuro Josic, Vienna (AT)

(73) Assignee: BIA Separations d.o.o., Ljubljana (SI)

( * ) Notice: Subject to any disclaimer, the term of this patent is extended or adjusted under 35 U.S.C. 154(b) by 0 days.

(21) Appl. No.: 09/601,037

(22) PCT Filed: Feb. 27, 1999

(86) PCT No.: PCT/EP99/01391

§ 371 (c)(1),
(2), (4) Date: Jul. 26, 2000

(87) PCT Pub. No.: WO99/44053

PCT Pub. Date: Sep. 2, 1999

(30) Foreign Application Priority Data

Feb. 27, 1998 (SI) .............................. P-9800058
Jul. 14, 1998 (SI) ............................ P-9800201

(51) Int. Cl.[7] .............................. B01D 15/08
(52) U.S. Cl. ................... 210/656; 210/198.2
(58) Field of Search ................ 210/635, 656, 210/198.2, 456

(56) References Cited

U.S. PATENT DOCUMENTS

| | | | | |
|---|---|---|---|---|
| 3,483,990 A | * | 12/1969 | Litle | 210/456 |
| 4,116,836 A | * | 9/1978 | DeAngelis | 210/198.2 |
| 4,627,918 A | * | 12/1986 | Saxena | 210/656 |
| 4,676,898 A | * | 6/1987 | Saxena | 210/198.2 |
| 4,895,806 A | | 1/1990 | Le et al. | 435/288 |
| 5,019,270 A | * | 5/1991 | Afeyan | 210/656 |
| 5,316,680 A | * | 5/1994 | Frechet | 210/635 |
| 5,522,994 A | * | 6/1996 | Frechet | 210/635 |
| 5,593,729 A | * | 1/1997 | Frechet | 427/337 |
| 5,633,290 A | * | 5/1997 | Frechet | 521/54 |
| 5,728,457 A | * | 3/1998 | Frechet | 210/635 |
| 5,929,214 A | * | 7/1999 | Peters | 530/417 |
| 5,972,218 A | * | 10/1999 | Josic | 210/321.78 |
| 6,319,401 B1 | * | 11/2001 | Josic | 210/456 |

FOREIGN PATENT DOCUMENTS

| | | | |
|---|---|---|---|
| DE | 4119203 A1 | 2/1992 | 210/198.2 |
| GB | 2 246 716 | * 12/1992 | 210/656 |
| WO | WO96/06158 | 2/1996 | 210/198.2 |

OTHER PUBLICATIONS

"SilicaROD—A new challenge in fast high–performance liquid chromatography separations" trends in analytical chemistry, vol. 17, No. 1, 1998, pp. 50–53.

* cited by examiner

Primary Examiner—Ernest G. Therkorn
(74) Attorney, Agent, or Firm—Jacobson Holman PLLC

(57) ABSTRACT

A porous self-supporting structure comprising at least two porous components A and B and the porous component B embraces the porous component A, wherein (i) surfaces of pores of the at least two porous components A and B are provided with chemical moieties for interaction with substances passing the pores and (ii) the pores of the porous components comprise a uniform multimodal pore size distribution through the entire polymeric structure.

21 Claims, 5 Drawing Sheets

CHROMATOGRAPHIC DEVICE

REFERENCE TO RELATED APPLICATIONS

This application is a 371 of PCT/EP99/01391 filed Feb. 27, 1999.

The invention pertains to a porous self-supporting structure comprising at least two porous components A and B, an article comprising a porous self-supporting structure comprising at least two porous components A and B, a housing for use in the article of the invention, end-fittings for use in the article of the invention as well as a process for manufacturing a porous self supporting structure of the present invention.

BACKGROUND OF THE INVENTION

Liquid chromatography is one of the most important tools for sample analysis as well as for the isolation or purification of compounds Chromatography works basically via an interaction of molecules dissolved in a liquid phase (mobile phase) and a solid phase (stationary phase). An almost ideal chromatographic process performs an efficient compound separation, sometimes of large sample volume, within very short time. A conventional chromatographic process is carried out by passing a liquid phase containing sample to be separated through a stationary phase (matrix). Since different compounds interact differently with the stationary phase the travelling time is different and as a consequence, a separation occurs. Conventional stationary phases are built in form of porous beads providing a high enough active surface for the interactions. They are packed in columns normally few centimeters long and few millimeters wads and fixed by porous frits on both ends. Because of their porosity and structure, the beads have rather low mechanical stability. When chromatographic separation systems are scaled up for commercial purposes, more matrix volume is required and thus large columns have to be employed. The combination of high flow rates and larger bed height (i.e. hydrostatic pressure) results in high pressure decrease across the matrix causing compression of the matrix material. This changes the column characteristics due to lower overall porosity and inhomogeneitics. One of the attempts to overcome this problem is incorporation of short columns with large cross-sectional area. However, uneven distribution of the sample over the cross-sectional area and a large dead volume still cause problems. The design of a chromatographic column using horizontal flow solves the problems related to the back pressure by employing a cylinder shaped column as disclosed by Saxena (U.S. Pat. Nos. 4,627,918, 4,676,898 and 4,840,730). The separation matrix is placed between two tube-shaped porous frits of different diameters. The mobile phase passes through the outer porous frit through the matrix. Since the height of the matrix bed is small the hydrostatic pressure does not play an important role. In addition, the bed thickness is low which causes only low back pressures.

Due to the particle structure however, two inherent drawbacks regarding efficiency and speed of the separation remain unsolved: neither the entire bed volume is used for the separation due to the voids (space between the particles) nor the separation time sufficiently short due to diffusion limitations inside one side closed particle pores.

A first attempt to overcome both of the above mentioned problems was introduced by Hjerten et. al J. Chromatogr., 473 (1989) 273–275, WO 90/07965 by polymerising a mixture of acrylic acid and methylenebisacrylamide for the production of a stationary phase. The resulting polymer plug contains channels which are large enough to permit a hydrodynamic flow. The polymer itself is, however, very soft and should by highly compressed before usage. On large scales, this leads to a drawback, since the compression produces non-uniform channels within the plus resulting in less than ideal column efficiency. Almost at the same time the so-called "membrane chromatography" war discovered by Svee et al. (U.S. Pat. Nos. 4,889,632 4,923,610 and 4,952,349). The used membranes have a rigid structure comprising bimodal pore-size distribution of open channels and as such excellent hydrodynamic characteristics resulting in short separation times. Although in principle the size of the membrane is non-limited, mechanical instability and irregular sample distribution limit the application of such units on large scale processes.

Another approach was introduced by Frechet and Svec (U.S. Pat Nos 5,334,310 and 5,453,185) by polymerising( monomers to a rigid porous plug within an empty chromatographic steel column of limited diameter. The porous plug has similar characteristics to those of the above mentioned membranes. The high back pressure of the plug however, determines the upper limit of the flow rate which together with a small column diameter prevents applications on preparative level. Josic et. al. disclosed rigid porous tubes based on methacrylates (WO-A-96/06158) where a mobile phase passes the bed in radial direction resulting in much lower back pressure even at elevated flow rates. This design enables a very fast separation on a semi-preparative level.

During tire bulk polymerisation of plugs of large diameter or tubes of large thickness a considerable amount of heat is generated Since the monomer mixture has a relatively low heat conductivity, the temperature within the mixture increases dramatically during the polymerisation (Peters E. C., F. Svec, J. M. J. Frechet, Chem. Mater., 9 (997) 1898) Since the pore size distribution is temperature dependent (Svec and Frechet, Chem. Mater., 7 (1995) 707), the resulting polymer has a variable structure and cannot be used for good chromatographic separations. Peters et. al., Chem. Mater., 9 (1997) 1898, suggested the polymerisation by slow addition of monomers mixture showing that the temperature increase is much lower and that the pore size distribution is only slightly affected, No separation efficiency of such a column however is presented. In addition, this approach prolongs the time for completion of the polymerisation and requires a very precise addition of the monomer mixture in order to avoid temperature increase.

Another way to control or decrease the amount of heat generated is the addition of polymeric particles of the same pore structure into the monomer mixture. Since the particle diameter is typically in the range of microns, monomers can diffuse into their pores and polymerise resulting in a non-homogeneous pore size distribution. To avoid changes in the polymer structure, pores of the particle should be filled with the inhibitors. If the concentration of the particles is too high, the inhibitor inhibits also the polymerisation of monomer mixture around the particles.

On the other hand, if the amount of polymeric particles added to the polymerisation mixture is too low, the particles can settle down in the mould during the polymerisation. In this way the local concentration of the particles in the monomer mixture in the upper part of the mould is low, thus the generated heat is again very large. It is therefore extremely difficult to prepare large porous polymers with a well defined pore size distribution.

Thus, it is an object of the present invention to produce a large scale rigid porous polymer media with well defined uniform pore characteristics.

It is further an object of the present invention to produce large scale rigid porous polymer media exhibiting low back pressures even at high flow rates.

It is still another object of the present invention to produce large scale rigid porous polymer media from large variety of monomers.

It is another object of the present invention to produce large scale rigid porous polymer media in an easy and inexpensive way.

These and further objects of the present invention will be evident from the following description of the present invention as well as from the given examples.

DISCLOSURE OF THE INVENTION

To achieve foregoing and other objects and in accordance with the purpose of the present invention as embodied and broadly described herein, the present invention is directed to a chromatographic unit comprising a porous polymer tube haling a large thickness and housing for the porous polymer tube. The resulting unit can be applied as a chromatographic column, for different bioconversion, adsorption and diagnostic processes as well as a matrix for peptide or oligonucleotide synthesis due to its ability to pass liquids therethrough. The porosity of the porous polymer tube is greater than about 0.2, preferably greater than 0.45. The porosity is defined in terms of water regain or mercury porosimetry.

The material contains small pores i.e. those below 200 nm in diameter, but also large pores of diameter of at least about 700 nm. The porous polymer tube is preferably a cylinder having the inner diameter of at least 1 mm and the outer diameter of at least 10 mm. The porous polymer tube can consist of a single monolith—single monolith porous polymer tube or of a set of tube-shaped monoliths inserted tightly one within another—multi monolith porous polymer tube. Each tube-shaped monolith can have different sorption properties, thus the sorption properties of the porous polymer tube can be tailored according the particular requirements. Also a single monolith porous polymer tube cap have different sorption properties due to a two step preparation preparation procedure described herein. The porous polymer tube of the invention is placed in a housing adjusted to the dimensions of the tube. The distributor and collector of the housing are designed to minimise dead volume of the whole unit. The housing can be produced from inert plastic materials e.g. polypropylene or Teflon® or from inert metal like stainless steel.

The porous polymer tube is produced from a mixture of monovinyl monomer and polyvinyl monomer in the presence of a porogen and an initiator. Different mixtures can be used for each tube-shaped monolith to obtain a predetermined characteristic. The predetermined characteristic may be e.g. a non-polar surface of the polymer tube. This can be achieved by introduction of e.g. $C_4$ or $C_{18}$ aliphatic groups. Also a polar surface may be desired. In this case different groups like hydroxyl or amino should be present. The thickness of the tube-shaped monolith wall should be established in such a way that during polymerisation the increase of temperature (reaction heat) within the mixture does not exceed the value that affects hydrodynamic characteristics of the final product. The height of the porous polymer tube however, is not limited.

In the case of formation of a multi monolith porous polymer tube, each tube-shaped monolith is polymerised separately in the way that the outer diameter of the inner tube-shaped monolith fits tightly to the inner diameter of the outer tube-shaped monolith. The thickness of the tube-shaped monolith can be different not exceeding however, the critical value affecting the pore structure. In the case of a single monolith porous polymer tube, preferably tube-shaped monoliths having a wall thickness less than critical are polymerised first. The outer diameter of inner tube-shaped monolith is slightly smaller than the inner diameter of the outer tube-shaped monolith. The tube-shaped monoliths are cylindrical and placed one inside the other, the voids in-between are filled with a monomer mixture. The monoliths can be linked together during the polymerisation resulting in a single monolith. After the porous polymer tube is prepared in one or the other way, porogens are washed out with suitable liquid.

DETAILED DESCRIPTION OF THE PREFERRED EMBODIMENTS

According to the invention a porous self-supporting structure is provided comprising at least two porous components A and B and the porous component B embraces the porous component A, wherein surfaces of pores of the at least two porous components A and B are provided with chemical moieties for interaction with substances passing the pores and the pores of the porous components comprise a multimodal pore size distribution through the entire polymeric structure.

Figure 9:
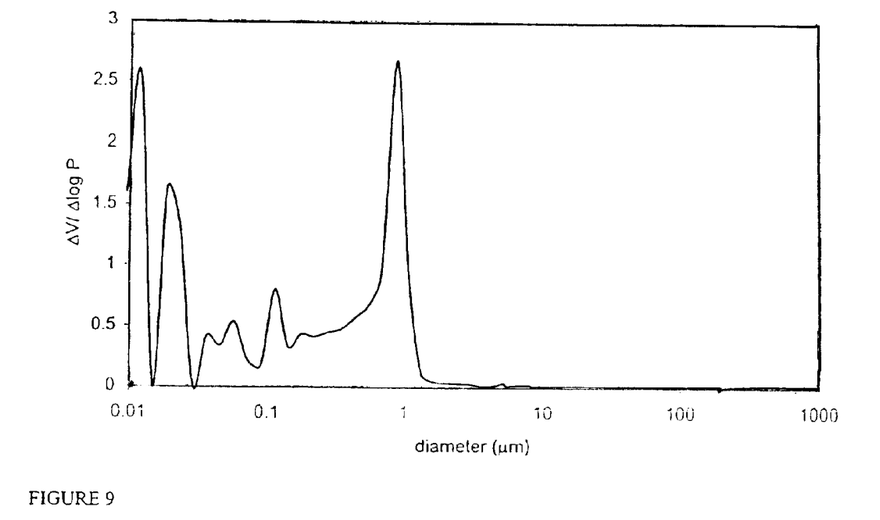
FIG. 9: Comparison of pore size distribution for inner and outer monolith or two-monolith tube

According to the invention the multimodal pore size distribution (FIG. 9) means at least three maxima of pore volume over a measured range of from 5 nm to 10 $\mu$m, which are separated by the regions where the pore volume is low or pores are absent at all. It offers the following advantages:

Pores With pore diameter above 700 nm exhibit low back pressure at elevate throughput Large number or pores with diameter below 700 nm providing high surface area necessary for high binding capacity.

The porous self-supporting structure of the invention comprises a polymer obtainable by polymerisation of monomers having at least two polymerisable moieties or two types of monomers, the first monomer type having one polymerisable moiety and the other monomer type is able to crosslink polymer chains obtained by polymerisation of the first monomer.

In a preferred embodiment of the porous self-supporting structure of the invention the surfaces of the pores are modified with functional groups such as ion-exchange groups, hydrophobic moieties, reactive groups for covalently binding of ligands such as affinity ligands, preferably proteins, enzymes, immunoglobulins, antigens, lectins, sugars, nucleic acids, cell organelles, or dyes, etc.

Preferably, the porous self-supporting structure of the invention utilises polyvinyl monomers and monovinyl monomers for their construction.

In particular, the group of polyvinyl monomers include divinylbenzene, divinylnaphtalene, divinylpyridine, alkylene dimethacrylates, hydroxyalkylene dimethacrylates, hydroxyalkylene diacrylates, oligoethylene glycol diacrylates, vinyl polycarboxylic acids, divinyl ether, pentaerythritol di-, tri-, or tetra methacrylate or acrylate, trimethylolpropane trimethylacrylate or acrylate, alkylene bis acrylamides or methacrylamides, and mixtures thereof.

According to the invention the group of monovinyl monomers include styrene, ring substituted styrenes wherein the substitution include chloromethyl, alkyl with up to 18 carbon atoms, hydroxyl, t-butyloxycarbonyl, halogen, nitro-, amino- groups, protected hydroxyls or amino groups, vinynaphtalene, acrylates, methacrylates vinylacetate and pyrrolidone, and mixtures thereof.

The polyvinyl monomer or polyvinyl monomer plus the monovinyl monomer are employed in the polymerisation mixture in an amount of 20 to 60% for the production of the porous self-supporting structure of the invention.

The first component B of the porous self-supporting structure of the invention comprises a tube like structure having an inner lumen 10 with an inner diameter 12 and an outer diameter 11 which lumen 10 is able to take up the second component A having an inner lumen 20 with an outer diameter 21 and an inner diameter 22 with the proviso that the outer diameter 21 of component A matches the inner diameter 12 of component B and component A is inserted in component B.

The component B can be of the same or different material, e.g. component A has anion exchange properties and B a reversed phase property.

Preferably, according to the invention the inner lumen 20 of component A serves as a sample collector.

The present invention is concerned also with an article comprising a porous self supporting structure and means for carrying out chromatographic processes. According to the invention the article is preferably a chromatographic unit 30, a column or a cartridge or a bioconversion reactor or matrix for peptide or oligonucleotide synthesis.

A preferred embodiment of the invention comprises a housing 36 providing a sample distributor 23 in which component D is arranged, the housing 36 having at least one inlet 41 and at least one outlet 40, an inner surface 42 and an outer surface 43 and a channel like structure or channel like structures 72 on the central part of its inner surface 42 forming a sample distributor 23, whereas the rest of the inner surface 42 is smooth.

Particularly preferred is a channel like structure 72 expressed as a helical or coiled groove 25 starting at the area of and being in direct contact with the inlet 41 of the chromatographic unit 30 and terminating after at least one complete turn but not in direct connection with the outlet 40 of the chromatographic unit 30. The article of the invention is in particular a chromatographic unit 30 further comprising a second end-fitting 38 and a first end-fitting 32, having O-ring 33,34,35,37 and tightening nuts 31,39.

In a preferred embodiment of the chromatographic unit 30 of the invention the first end-fitting 32 has a top part 62, a bottom part 63 and a casing, the first end-fitting 32 is essentially of cylindrical shape, the first end-fitting 32 comprises a collar 61 dividing the cylindrically shaped end-fitting 32 into two parts 62,63, whereby the part of the end-fitting 32 nearest to the collar 61 is the bottom part 62 comprising a connector 60 in connection with a central bore 64 extending through the entire first end-fitting 32 and an O-ring 35 placed in a ring-like groove in the casing at the area of the top part 63 of the first end-fitting 32 and 0-rings in circular grooves in the top part 63 of the first end-fitting 32.

In a preferred embodiment of the chromatographic unit 30 of the invention tile second end-fitting 38 has a top part 52, a bottom part 53 and a casing, the second end-fitting 38 is essentially of cylindrical shape, the second end-fitting 38 comprises a collar 51 dividing the cylindrically shaped end-fitting 38 into two parts, whereby the part of the end-fitting 38 nearest to the collar 51 is the top part 52 comprising a connector 50 in connection with a dead-end central bore 54 communicating with a bore 55 which is perpendicular to the dead-end central bore 54, the bore 55 starts in a ring-like groove 56 at the surface of the casing of the second end-fitting 38 and leads into the dead end central bore 54.

A housing 36 for use in the article of claim 13 providing a sample distributor 23 wherein the channel like structure 72 is a helical or coiled groove 25.

As already explained, the component A is inserted into component B. In the case that component A still has a relatively large inner lumen 20 thus would lead to a relatively large dead volume in the whole chromatographic unit. In order to reduce or avoid this drawback, it is possible to insert a collecting element 80 into the component A. The collecting element matches the inner lumen of component A by either fitting tightly into the inner lumen or leaving a gap. When a gap is formed between the collecting element 80 and the inner lumen 20 of component A, this gap is able to work as sample collector and simultaneously rendering the dead volume significantly smaller. In the case that the collecting element fits tightly into component A, of course means must be provided which lead to removal of the liquid running through the porous components A and B. This can be done by providing the outer surface of the collecting element 80 with channels or channel-like structures. Preferably, the channels or channel-like structures 82 are formed by a helical or coiled groove 81. The collecting element having a top part 84 and a bottom part 85 provides on its top part 84 an unstructured surface, preferably a smooth surface. However, the bottom part 85 comprises a channel 83 which extends inwardly from the outer side preferably to the center. The channel-like structure 82 prolongs into the channel 83 on the bottom part 85 of the collecting element 80. Preferably the channel 83 communicates with the bore 64 of the first end-fitting 32. The top part 84 contacts bottom part 53 of the second end-fitting 38.

Figure 1:
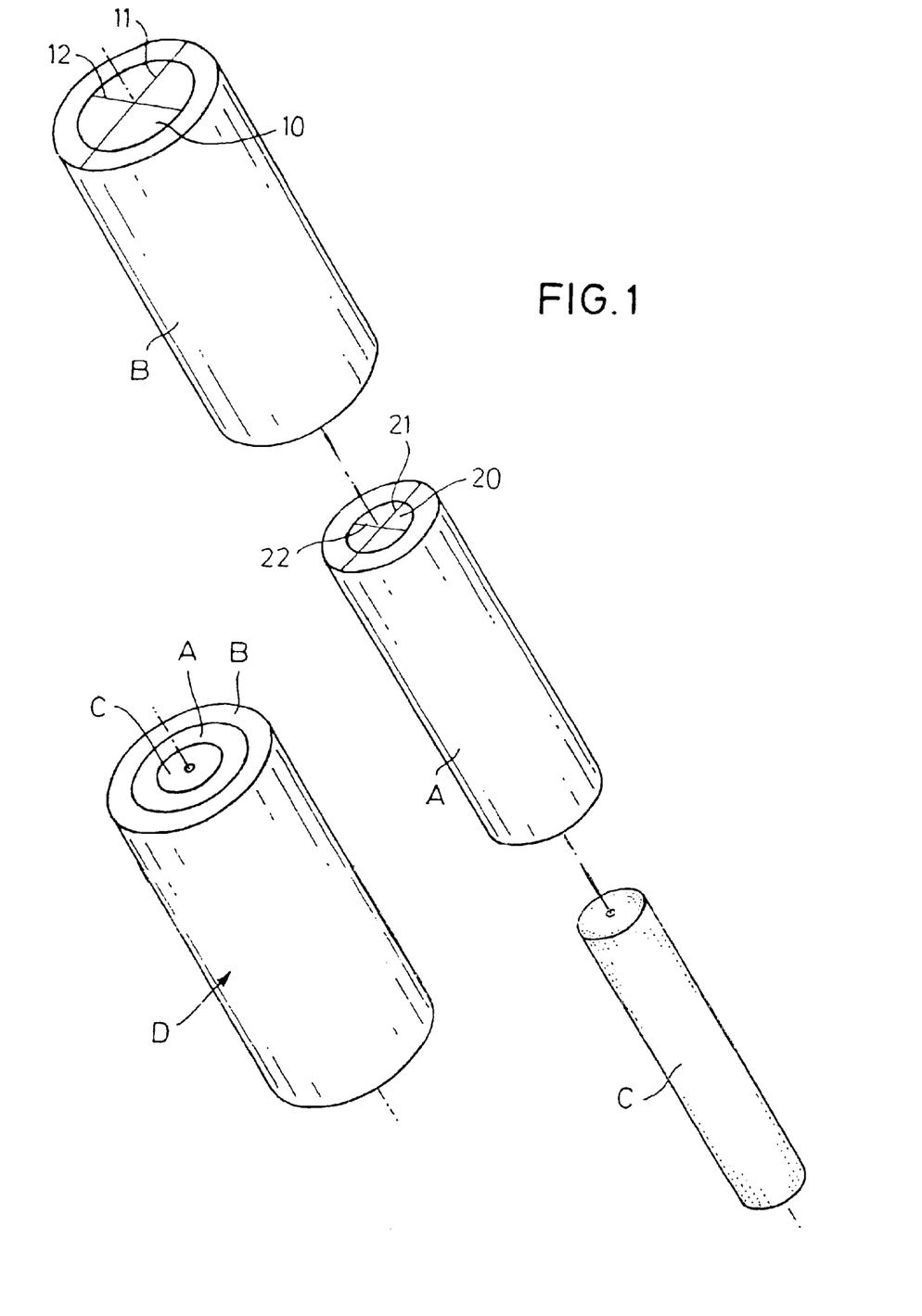
FIG. 1: Schematic view of the assembly D, the porous polymer tube, of component A, B and a component C
Figures 2, 3:
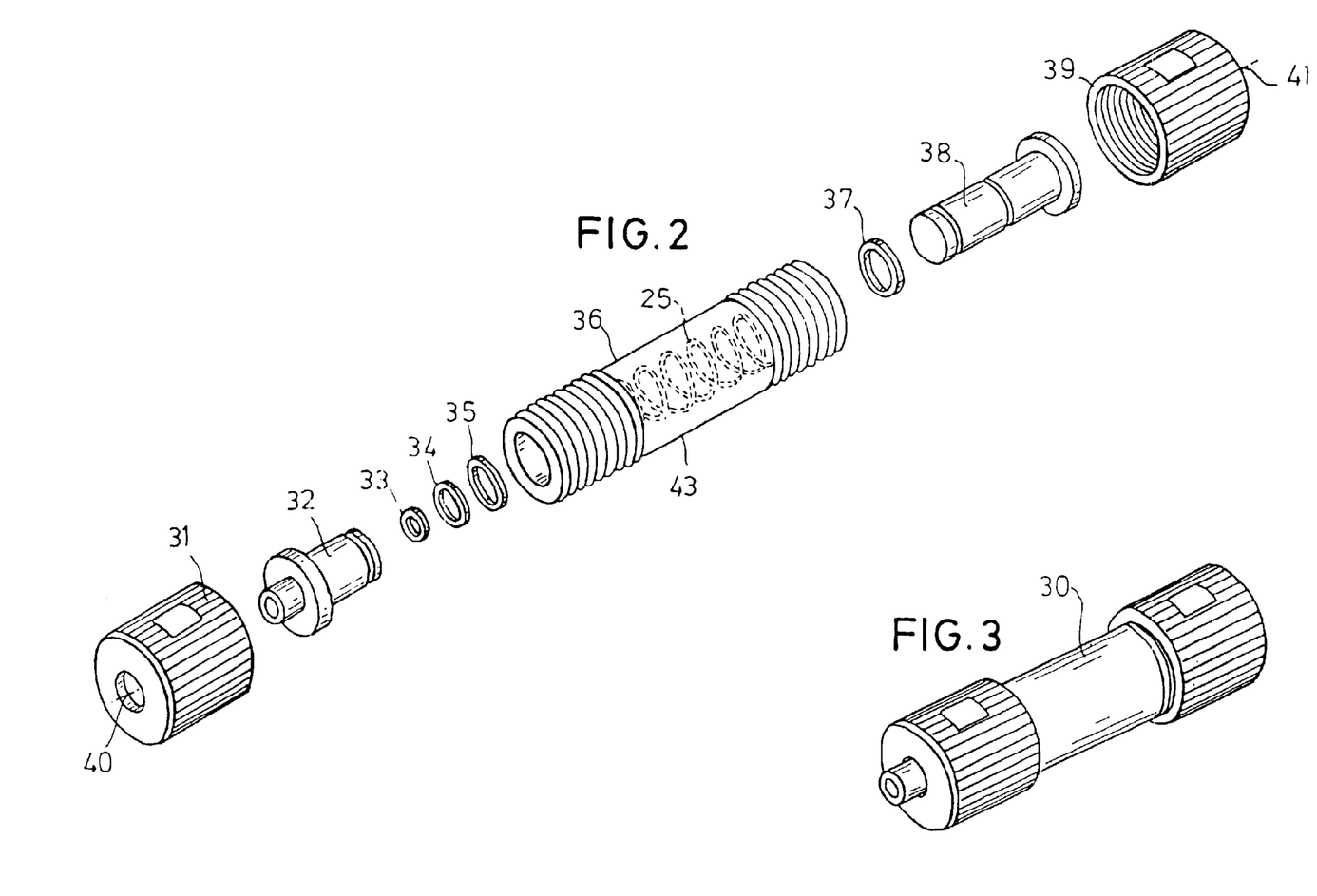
FIG. 2: Technical drawing of the housing
FIG. 3: View of the chromatographic unit
Figure 8:
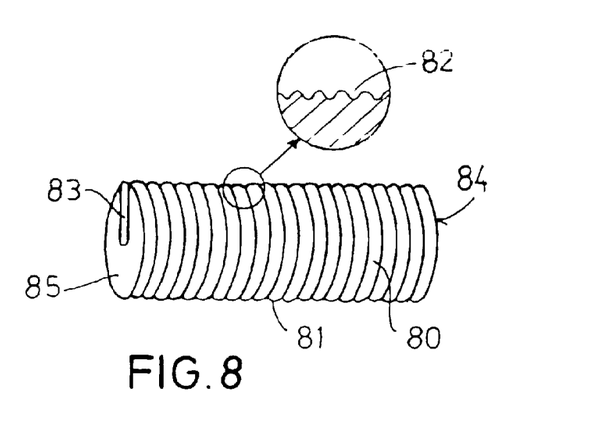
FIG. 8: A collecting element for reducing the dead volume

The chromatographic unit 30 presented herein comprises all parts from FIG. 2, optionally an clement 80 from FIG. 8 and a porous polymer tube D presented in FIGS. 1 to 6. The housing is preferably made of inert plastic materials e.g. polypropylene or Teflon® or from inert metal like stainless steel. Not all the parts have to be made from the same material.

FIG. 1 shows an assembly D, the porous polymer tube, of three different components, component A, component B and component C. The three components can be inserted into each other to form a multi monolith porous polymer tube, wherein component C forms the most inner part, component A the middle part and component B the outer part of the concentric assembly D. Component B comprises an inner lumen 10 which diameter 12 is large enough to match the outer diameter 21 of component A. In order to have component C inserted into component A of course the diameter of C has to match the inner diameter 22 of component A. Component C finally comprises a central bore extending through the entire length of component C. The central bore works as sample collector in the assembly D of FIG. 1. If the central bore has larger diameter an element 80 from FIG. 8 can be inserted to minimise a dead volume of the collector as well as to provide additional mechanical stability.

FIG. 2 shows an exploded view of the chromatographic unit 30 of FIG. 3. The chromatographic unit consists of tightening nuts 31 and 39 comprising corresponding openings 40 and 41 respectively. The tightening nuts are screwed on the housing 36 in order to keep together the components 32,33,34,35, a multi or single monolith porous polymer tube such as assembly D in the housing 36 as well as the components 37 and 38. Component 32, the first end-fitting, and the second end-fitting 38 is placed at the opposite end. The second end-fitting is inserted into the housing 36 and sealed with the O-ring 37 in the middle part of the fitting 38. The O-ring 37 fits into the groove in the middle of the casing of end-fitting 38. The first end-fitting 32 is inserted into the housing 36 and sealed with the O-rings 33,34 and 35.

Figure 4:
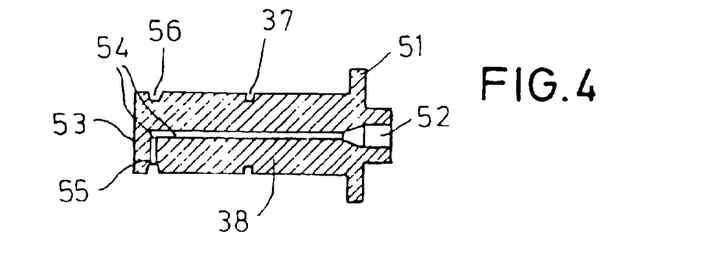
FIG. 4: Second end-fitting

FIG. 4 shows the second end-fitting 38 having a top part 52 and a bottom part 53 and a casing. The end-fitting 38 is of cylindrical shape and has a collar 51 which divides the cylindrically shaped end-fitting 38 unsymetically into two parts. The longer part is inserted into the housing 36 whereby the collar 51 prevents the end-fitting to slide completely into the housing 36. The width of the collar 51 is matching the outer diameter of the housing 36 so that the tightening nut 39 can be screwed over the collar 51 and the housing 36 to fix end-fitting 38. The end-fitting 38 has a central bore which has a dead-end at the lower part of the end-fitting 38 in the area of the bottom part 53. A bore 55 which is perpendicular to the central bore 54 meets the central bore 54. A flow entering the chromatographic unit at the connector 50 runs through the central communicates with a groove 56 which is circular-shaped.

Figure 5:
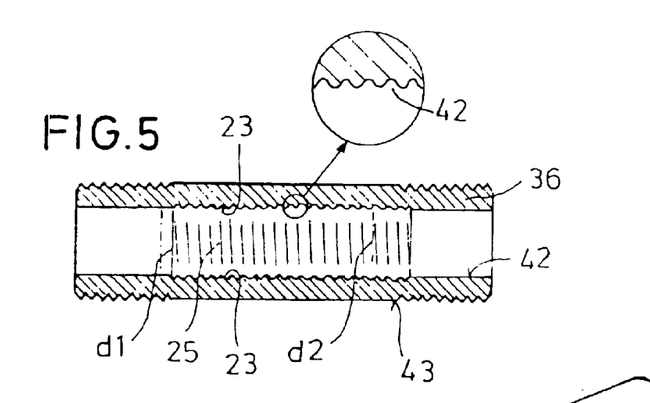
FIG. 5: A housing according to the invention
Figure 6:
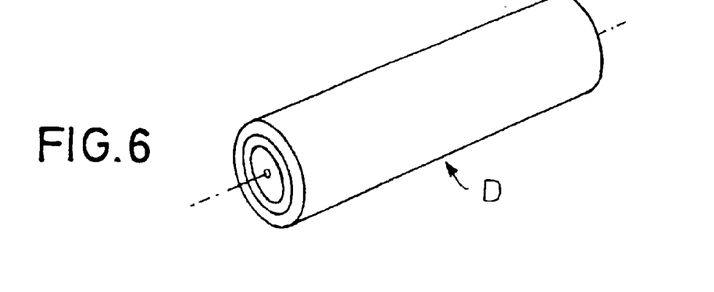
FIG. 6: A component D, the porous polymer tube, of the invention

FIG. 5 shows the situation in the housing. Component D of FIGS. 1 and 6 is placed in the housing 36 in such a way that the bottom part matches the end of distributor 23, but distributor 23 extends over the top of the component D. The position of the component D inside the housing 36 is indicated with dotted lines d1 and d2. The central part of inner wall 42 of the housing 36 shows grooves in a helical or coiled arrangement forming a sample distributor 23. The end-fitting 38 is inserted to touch the component D and communicates with the helical or coiled grooves 25 so that a liquid entering the housing through the bore 55 and the ring groove 56 is lead through the helical or coiled groove 25 at the inner surface 42 of the housing 36 to the outer side of the component D. The O-ring 37 of the end-fitting 38 lies above groove 25 of the distributor 23 and seals the inner surface 42. However, the coiled or helical groove 25 does not communicate with the central bore of the end-fitting 32 shown in FIG. 7. Therefore, the liquid has to pass the assembly D which is a porous polymer tube. In the central bore of the porous polymer tube working as a collector and optionally comprising the element 80 of FIG. 8, the liquid is collected and guided to the central bore 64 of the end-fitting 32.

FIG. 6 shows schematically a component D, the porous polymer tube, which is placed in FIG. 5.

Figure 7:
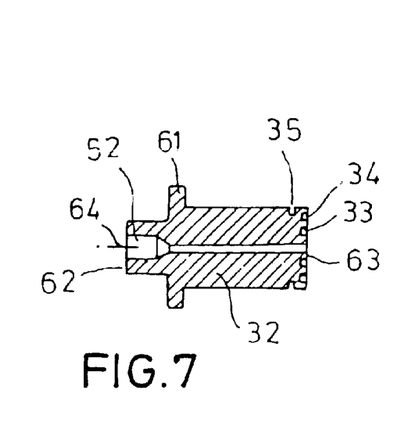
FIG. 7: A first end-fitting of the invention

FIG. 7 shows the first end-fitting 32 which has an analogous shape as the first end-fitting in regard to the collar 61, a casing connector 60 as well as the top part 62 and bottom part 63. However, the central bore 64 extends through the middle of the end-fitting and through its entirety. At the bottom part of the end-fitting 32 O-rings 35,34 and 33 are sealing the end-fitting and the housing 36. The liquid coming from the central bore of the porous polymer tube is guided through the central bore 64 and can be collected.

FIG. 8 shows the collecting element 80 having on its outer surface channels or a channel like structure 82 forming a helical or coiled groove collector 81. The top part 84 is smooth, whereas the bottom part 85 comprises a channel 83 extending from the outer side to the center. The channel like structure 82 prolongs into the channel 83 on the lower part 85 of the collecting element 80. The channel 83 communicates with the bore 64 of the first end-fitting 32. The top part 84 touches bottom part 53 of the second end-fitting 38.

The porous polymer tube is produced from a mixture of monovinyl monomer(s) and polyvinyl monomer(s) in the presence of a porogens and optionally an initiator. The polymer contains small pores i.e. those below 200 nm in diameter, but also large pores of diameter at least about 700 nm. The porosity of the polymer is greater than about 0.2, preferably greater than 0.45. Different mixtures can be used for each tube-shaped monolith to obtain desired characteristics. The thickness of the wall of the tube-shaped monolith is preferably established in such a way that during the polymerisation, the increase of the temperature within the mixture does not exceed the value that affects hydrodynamic polymer characteristics negatively. The typical thickness of the tube-shaped monolith obtained in one step polymerisation ranges from few millimetres to few centimetres.

The acceptable temperature range of the polymerisation reaction is determined by performing polymerisation of equal monomer mixtures in a thin sheet-shape mould. The thickness of the mould is preferably such that by measuring the temperature in the middle of the monomer layer during the polymerisation, preferably only a slight or more preferred no temperature increase is detected. Each polymerisation is preferably performed at substantially constant polymerisation temperature, higher of the lowest temperature found to be optimal regarding the sorption properties related to the optimal hydrodynamic characteristics for particular polymer. The hydrodynamic characteristics of the polymer are determined by measurement of pore size distribution with mercury porosimetry, porosity again by mercury porosimetry or by water regain and by measurement of back pressure vs. flow rate. The highest temperature where the characteristics remain unchanged is considered as the upper allowable temperature limit.

The upper value of the thickness of the tube-shaped monolith can be established in a way that tube-shaped moulds of different thickness are prepared and filled with monomer(s) mixture. During the polymerisation, the temperature in the middle of the monomer(s) mixture layer is recorded. The temperature during the polymerisation should not exceed the value of the upper allowable limit, in order to obtain a monolith suitable for good performing chromatography.

Besides the above mentioned matters, another approach for the determination of tube-shaped monolith thickness is possible. In this case a thick tube-shaped mould is filled with monomer(s) mixture and temperature at different distances from the mould wall is recorded. In this way, a dynamic temperature profile inside the polymerisation mixture is obtained. By deriving equations for particular geometry based on heat balances, the generated specific heat and heat conductivity coefficients can be calculated. Based on this data, a temperature increase inside the tube-shaped mould of defined thickness can be calculated. Furthermore, using the upper allowable temperature limit, a maximal mould thickness can be calculated.

Once the mould thickness for a particular monomer mixture is determined in one or another way, tube-shaped moulds of different inner and outer diameter, but defined difference in-between, can be prepared.

For the preparation of multi monolith porous polymer tube, the tube-shaped monoliths are preferably prepared in a way that the inner porous polymer tube-shaped monolith fits sightly into the outer porous polymer tube-shaped monolith. The height of all tube-shaped shaped monoliths is not limited but is preferably the same The number of tube-shaped monoliths is basically unlimited and thus multi monolith porous polymer tube of any desired diameter can be obtained.

For the preparation of a single porous polymer tube however, the tube-shaped monoliths are preferably prepared in a way that all are of equal height and the outer diameter of inner porous polymer tube-shaped monolith is smaller than the inner diameter of the outer porous polymer tube-shaped monolith. In this way there is a void space between the porous polymer tube-shaped monoliths. This space can be filled afterwards with the monomer mixture and polymerisation is performed for the second time or left untreated. The thickness of the void space is again limited by the upper allowable thickness determined for the tube-shaped monoliths. During the polymerisation the different porous polymer tube-shaped monoliths are linked together to form a single porous polymer tube of desired diameter.

Polyvinyl monomers include divinylbenzene, divinylnaphtalene, divinylpyridine, alkylene dimethacrylates, hydroxyalkylene dimethacrylates, hydroxyalkylene diacrylates, oligoethylene glycol diacrylates, vinyl polycarboxylic acids, divinyl ether, pentaerythritol di-, tri-, or tetra methacrylate or acrylate, trimethylolpropane trimethylacrylate or acrylate, alkylene bis acrylamides or methacrylamides, and mixtures of any such suitable polyvinyl monomers.

Monovinyl monomers include styrene, ring substituted styrenes wherein the substitution include chloromethyl, alkyl with up to 18 carbon atoms, hydroxyl, t-butyloxycarbonyl, halogen, nitro, amino group, protected hydroxyls or amino groups, vinylnaphtalene, acrylates, methacrylates vinylacetate and pyrrolidone, and a mixture thereof. The polyvinyl monomer or polyvinyl monomer plus the monovinyl monomer are generally present in the polymerisation mixture in an amount of 20 to 60%.

The porogens can be selected from different type of material like aliphatic hydrocarbons, aromatic hydrocarbons, esters, alcohols, ketones, ethers, solution of soluble polymer, and mixture thereof.

Soluble polymers may also be added to the monomers. They are dissolved from tile polymer after its formation and serve for increase of porosity. If they are present, then preferably in an amount of 10 to 40%.

For polymerisation initiation conventional free-radicals generating initiators can be used such as azo compounds e.g. azobisisobutyronitrile and 2,2'-azobis(isobutyramide) dihydrate or peroxides e.g. benzoyl peroxide and dipropylperoxydicarbonate. Different initiators may be used to obtain a different pore structure related to the degradation rate of the initiators. The amount of initiator is typically in the range of from about 0.5 to 4% by weight of the monomers.

Before the polymerisation mixture is placed in the mould it is preferably deaerated by means of inert gas like nitrogen or argon to remove or displace as much oxygen as possible Once it is prepared the mould is preferably sealed to prevent contamination with air.

The polymerisation is e.g. carried out in a conventional manner known to the skilled person, generally at a temperature of from about 50° to 90° C. for a period up to 48 hours. Preferably the temperature is accurately regulated to obtain defined pore size distribution all over the polymer in a controlled and reproducible manner.

After the porous polymer tube has been formed, it is washed to remove any porogenic solvent as well as to dissolve any soluble polymers, if present. The type of solvent is not critical. Many different solvents can be used, such as methanol, ethanol, benzene, toluene acetone or tetrahydrofuran. To remove the porogens and dissolved polymers completely, the washing step should be repeated several times.

If the polymer tube is to be modified with certain functional groups, the polymer can be treated with certain chemical compounds. In the case of glycidyl methacrylate (as one monomer for making the polymer) which contains epoxy groups, the polymer can further react with an olcum 1,4-dioxan mixture to give sulfonic groups (SP), chloroacetic acid to give carboxymethyl groups (CM) or different amines like diethylamine to give N,N-diethylamino-2-hydroxypropyl groups (DEAHP), triethylamin hydrochloride for quaternary trimethylamino groups (Q) or ethylenediamine for introduction of amino groups (EDA). Hydrophobic groups may be introduced using alcoholates like sodium ethanolat, butanolat or octanolat. The polymer may also react with affinants for specific binding. Affinants can be, but are not limited to, proteins, enzymes, antibodies, antigens, lectins, sugars, dyes, nucleic acids or cell organelles. The polymers based on other monomers can also be treated in analogous ways which are known to the skilled person.

For the preparation of a multi monolith porous polymer tube, the tube-shaped monoliths are washed to remove the porogenic solvent as well as to dissolve any soluble polymers present. If no further modification of the tube-shaped monoliths is required or all the tube-shaped monoliths should bear the same functional groups the tube-shaped monoliths are inserted one into another to form multi monolith porous polymer tube. The additional functional groups can be introduced using one of above described reagents. Finally, the multi monolith porous polymer tube is placed in a housing. If each or at least two of the tube-shaped monoliths should bear different functional groups, the modification should be performed on each tube-shaped monolith separately and only afterwards, be inserted one into another to form a multi monolith porous polymer tube. Another approach is to modify at first the outer tube-shaped monolith. After the modification reaction is completed the unreacted reagent is washed out and smaller tube-shaped monolith is inserted. The assembly can be placed in a neon different reagent. Since the reactive groups of the larger tube-shaped monolith are already converted, the reaction is performed only in the smaller tube-shaped monolith. This procedure can be repeated several times, depending on the number of tube-shaped monoliths.

For the preparation of single monolith porous polymer tube, when no further modification of the tube-shaped monoliths or equal functional groups should be introduced to all the tube-shaped monoliths, they are inserted concentrically in a mould one into another. A monomer mixture previously deaerated is added to fill all voids between the tube-shaped monoliths except a central bore. The mould is sealed and the polymerisation is performed at the same temperature as the tube-shaped monoliths were prepared. After the polymerisation is completed, the single monolith porous polymer tube is washed to remove any porogenic solvent as well as to dissolve any soluble polymers present. If required, functional groups can be introduced into the polymer using the described reagents supra. Finally, the tube is placed in a housing and the unit is ready to be used.

When a single monolith porous polymer tube with different functional groups is to be prepared, the following ways of preparation are possible. If the required functional groups are part of the monomers and different from the one the tube-shaped monoliths were prepared of, a similar procedure is used as in the case of the preparation of the single monolith porous polymer tube with no further modification. The polymerisation temperature may however be different from the one employed during the tube-shaped monolith preparation. Another approach is used, if the functional groups should be introduced into the polymer tube-shaped monolith. The tube-shaped monoliths should firstly be washed to remove any porogenic solvent as well as to dissolve any soluble polymers present. To each, or a set of tube-shaped monoliths the required functional groups are introduced as described above. The tube-shaped monoliths are dried and emerged into the porogen mixture or inert substance which fills the pores and can easily be removed afterwards. In this way the pores are filled and any additional polymerisation within them is slowed down or even inhibited completely. The tube-shaped monoliths prepared in this way are inserted in the mould and processed according to the procedure described for the preparation of the single monolith porous polymer tube with uniform sorption characteristics. Finally, the tube is washed, placed in a housing and the unit is ready to be used.

The present invention will further be explained by the following non-limiting examples.

EXAMPLES

Example 1

Preparation of a Chromatographic Unit Comprising Multi Monolith Polymer Porous Tube Two stainless steel moulds were prepared. The first mould comprises of two stainless steel tubes, outer of inner diameter 35 mm and inner of outer diameter 17.6 mm. The stainless steel tubes have wall thickness of 1.5 mm and having a very high coefficient of heat conductivity. The smaller tube was inserted in the middle of the larger one. The stainless tube with smaller diameter is longer then the stainless tube with larger diameter in order to allow the flow-through of the thermostated liquid with the purpose of removing generated heat. One nut seals the area between inner and outer tube to form a cylindrical shape void in which monomer mixture is placed. A second nut seals the same area on the upper side. This nut has a septum through which the monomer mixture is injected into the mould and a small hole for air to exit during the loading of the monomer mixture. After filling is completed the hole is sealed to prevent air to enter. The second mould is constructed in the similar way with the inner diameter of outer tube of 17.5 mm and the outer diameter of the inner tube of 1.2 mm. A monomer mixture was prepared by mixing glycidyl methacrylate, ethylene dimethacrylate, cyclohexanol, dodecanol and benzoyl peroxide. The mixture was bubbled with nitrogen for 20 minutes to remove any oxygen present. The mixture was injected into the mould until it was completely filled and the polymerisation was started by placing both moulds into a thermostated water bath. After 16 hours the moulds were removed from the bath, cooled to room temperature and the nuts were removed. The tube-shaped monoliths were taken from the moulds and placed in pure methanol. The methanol was changed several times to remove the porogens. The small tube-shaped monolith was then inserted into the hole of the larger one and placed in the appropriate housing.

Example 2

The multi monolith porous polymer tube of two tube-shaped monoliths was prepared according to the example 1. For each tube-shaped monolith pore size distribution using mercury porosimetry was measured. Both measurements give very similar multimodal pore size distribution presented in FIG. 9.

Example 3

Figure 10:
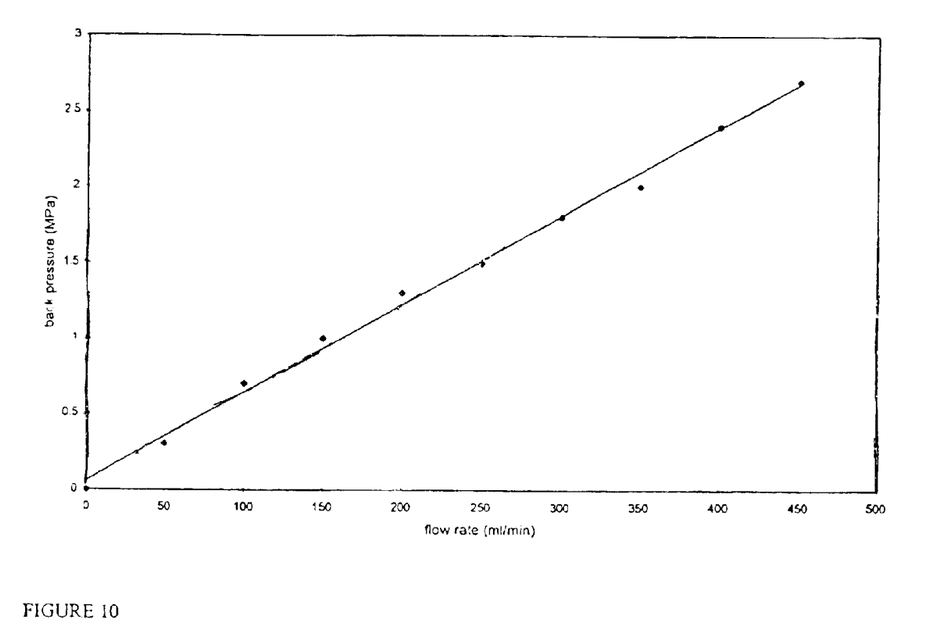
FIG. 10: Relation between back pressure and a flow rate

The chromatographic device was prepared according to the example 1. The device was connected to the HPLC preparative system and tested under different flow rates up to 450 ml/min. The device exhibits low back pressure even at elevated flow rates. The relationship between back pressure and flow rate was found to be linear (FIG. 10).

Example 4

Preparation of Reverse Phase Multi-monolith Tube

The moulds described in the example 1 were used. A monomer mixture was prepared by mixing glycidyl methacrylate, stearyl methacrylate, ethylene dimethacrylate, cyclohexanol, dodecanol and benzoyl peroxide. The mixture was bubbled with nitrogen for 20 minutes to remove any oxygen present. The mixture was injected into the mould until it was completely filled and the polymerisation was started by placing both moulds into thermostated water bath. After 16 hours the moulds were removed from the hath, cooled to room temperature and the nuts were removed. The polymer cylinders were taken from the moulds and placed in pure methanol. The methanol Ad as changed several times to remove the porogens. The small tube-shaped monolith was then inserted into the hole of the larger one and placed in the appropriate housing. The multi monolith porous polymer tube exhibits strong hydrophobic character.

Example 5

Preparation of Chromatographic Unit Comprising Single Monolith Polymer Porous Tube Two stainless steel moulds similar to the ones in example 1 but with different dimensions of void diameters were used for the polymerisation of two tube-shaped monoliths. The inner diameter of larger tube-shaped monolith was 2 mm larger of the outer diameter of the smaller The smaller was removed from the mould. The larger tube-shaped monolith was left in the mould from which the inner stainless tube was removed. The mould was sealed from one side with the nut. The smaller tube-shaped monolith was inserted into the hole of the large one remained in the mould. The mould was sealed also on the other side with the septum through which a deaerated monomers mixture from example 1 was added to fill the void between two monolith cylinders. The mould was placed into thermostated bath for 20 hours. After the polymerisation was completed the single monolith porous polymer tube was removed. The monomers were polymerised mixture between two tube-shaped monoliths and inserted to give a single monolith porous polymer tube.

Example 6

Separation on Chromatographic Unit Comprising Multi Monolith Porous Polymer Tube The multi monolith porous polymer tube was prepared according to example 1. The housing containing the multi monolith porous polymer tube was filled with pure diethylamine and left to react for 24 hours at the temperature of 30° C. After the reaction was completed, the excess of diethylamine was removed by pumping through the multiply monolith porous polymer tube water at the flow rate of 5 ml/min. The tube was finally washed with 20 mM Tris-HCl buffer pH=7.4.

A Solution of myoglobin (5 mg/ml), conalbumin (10 mg/ml) and trypsin inhibitor (20 mg/ml) in 20 mM Tris-HCl buffer, pH=7.4 was injected through the loop of 500 µl.

Figure 11:
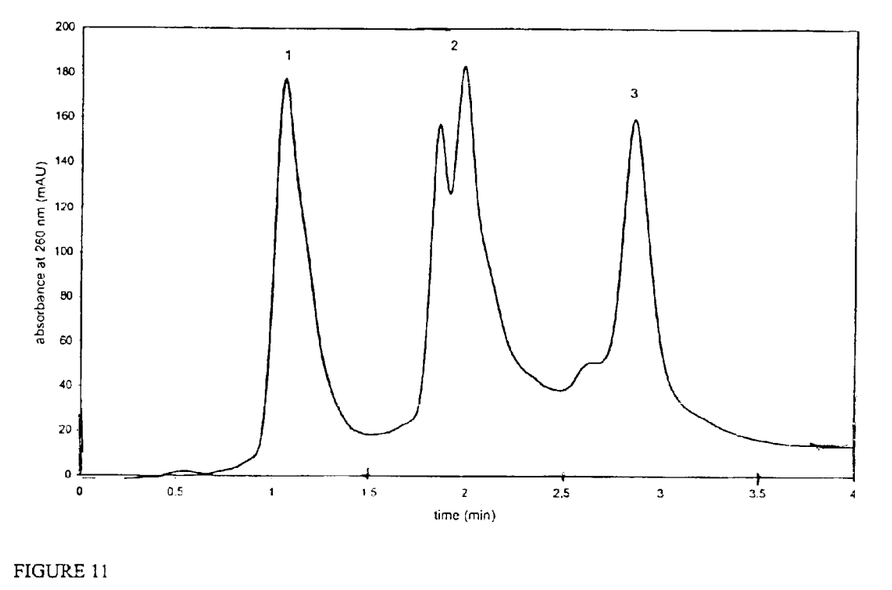
FIG. 11: Separation and purification on multi-monolith tube containing DEAE and affinity active groups
Figure 12:
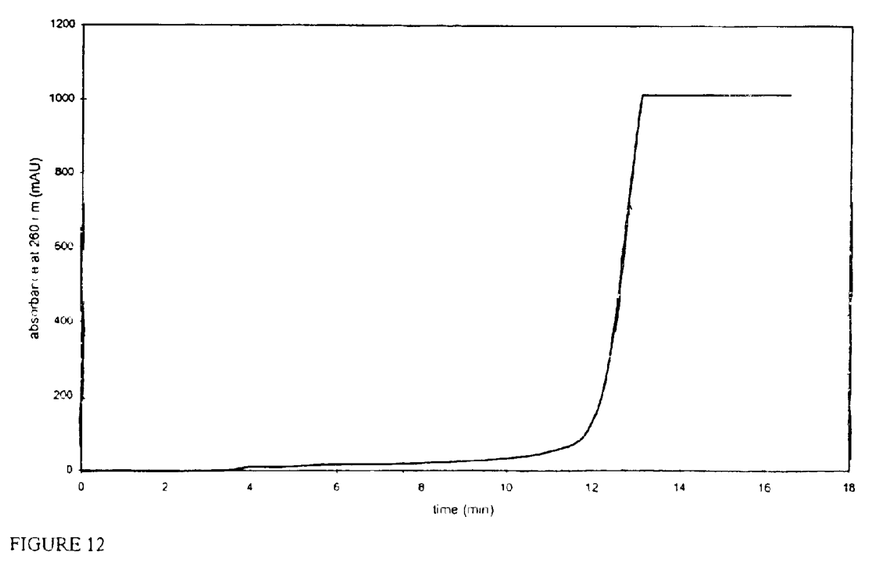
FIG. 12: Break-through curve of capacity measurement on 50 ml multi-monolith tube.

Binding buffer was 20 mM Tris-HCl buffer., pH=7.4 and eluting buffer was 20 mM Tris HCl buffer+1M NaCl, pH=7.4. The following separation method was applied: 45 seconds with 100% buffer A, gradient from 100% to 20% buffer A within 3 minutes. Flow rate was 42 ml/min. The separation was followed on UV spectrophotometer at 280 nm and the respective chromatogram is shown in FIG. 11. In addition, protein binding capacity was measured. The solution of human serum albumin (11 mg/ml) was dissolved in 20 mM Tris-HCl buffer, pH=7.4 and pumped through the multi monolith porous polymer tube with the flow rate of 10 mil/min. The capacity estimated from the break-through curve presented on FIG. 12 was around 1 g of protein.

Example 7

Preparation of Chromatographic Unit Comprising Multi Monolith Porous Polymer tube Containing Different Functional Groups Two tube-shaped monoliths were prepared using the moulds and procedure described in example 1. Both were placed into pure methanol. The methanol was changed several times to remove the porogens. Finally, the tubes were placed in the mixture of methanol and water 50:50 and in the distilled water. After the washing step was completed, the larger tube-shaped monolith was placed in pure diethylamine at the temperature of 30° C. After 24 hours the tube was removed and placed in distilled water. The water was changed several times to remove all diethylamine from the pores.

The smaller tube-shaped monolith was placed in the immunoglobulin solution (2 mg/ml of IgG in 0.5 phosphate buffer. pH 8.0) at room temperature. After 24 hours the tube was placed in distilled water which was changed several times. to remove remaining protein. The smaller tube-shaped monolith was inserted into the hole of the large one to form multi monolith porous polymer tube and placed in the housing.

Sample of myoglobin (5 mg/ml), conalbumin (10 mg/ml) trypsin inhibitor (20 mg/ml) and protein A (10 mg/ml) in 20 mM Tris-HCl buffer, pH=7.4 was injected through the 500 µl sample loop.

Binding buffer was 20 mM Tris-HCl buffer, pH=7.4, eluting buffer from DEAE groups was 20 mM Tris-HCl buffer+1M NaCl, pH=7.4 and eluting buffer from affinity groups was 0.5 M acetic acid, pH=2.5.

All the proteins adsorb on the outer part of the multi monolith porous polymer tube on DEAE groups in ion-exchange mode. After applying salt gradient described in example 6 all proteins arc selectively eluted. Since the IgGs bind selectively only protein A, other proteins are eluted out of the multi monolith porous polymer tube. Protein A however binds to the inner part of the multi monolith porous polymer tube and cannot be eluted with the salt gradient since the bond is based on affinity interaction. The protein A is released with the pH change. Using a multi monolith porous polymer tube containing different active groups one can perform separation and purification within single run.

What is claimed is:

1. A porous self-supporting structure comprising a tube having at least two porous components A and B and the porous component B embraces the porous component A, wherein i) surfaces of pores of the at least two porous components A and B are provided with chemical moieties for interaction with substances passing the pores and ii) the pores of the porous components comprise a uniform multimodal pore size distribution through the entire polymeric structure, wherein the first component B comprises a tube like structure having an inner lumen (10) with an inner diameter (12) and an outer diameter (11), the lumen (10) is able to take up the second component A having an inner lumen (20) with an outer diameter (21) and an inner diameter (22) with the proviso that the outer diameter (21) of component A matches the inner diameter (12) of component B and component A fits in component B.

2. The porous self-supporting structure of claim 1 wherein the structure comprises a polymer obtainable by polymerisation of monomers having at least two polymerisable moieties or two types of monomers the first monomer type having one polymerisable moiety and the other monomer type is able to crosslink polymer chains obtained by polymerisation of the first monomer.

3. The porous self-supporting structure of claim 2, wherein the monomers are polyvinyl monomers or polyvinyl monomers plus monovinyl monomers.

4. The porous self-supporting structure of claim 3, wherein the polyvinyl monomers arc divinylbenzene divinylnaphthalene, divinylpyridine, alkylene di methacrylates, hydroxyalkylene dimethacrylates, hydroxyalkylene, diacrylates, oligoe thylene glycol diacrylates, vinyl polycarboxylic acids, divinyl ether, pentaerythritol di-, tri-, or tetra methacrylate or acrylate, trimethylolpropane trimethylacrylate or acrylate, alkylene bis acrylamides or methacrylamides, or mixtures thereof.

5. The porous self-supporting structure of claim 3, wherein the monovinyl monomers are styrene, ring substituted styrenes wherein the substitutions are chloromethyl, alkyl with up to 18 carbon atoms, hydroxyl, t-butyloxycarbonyl, halogen, nitro-, amino- groups, protected hydroxyls or amino groups, vinylnaphthalene, acrylates, methacrylates, vinylacetate, or pyrrolidone, or mixtures thereof.

6. The porous self-supporting structure of claim 5, wherein the polyvinyl monomers or polyvinyl monomers plus the monovinyl monomers art present in the polymerisation mixture in an amount of 20 to 60%.

7. The porous self-supporting structure of claim 1, wherein the surfaces of the pores are modified with functional groups, hydrophobic moieties, reactive groups for covalently binding of ligands, enzymes, inmunoglobulins, antigens, lectins, sugars, nucleic acids cell organelles, or dyes.

8. The porous self-supporting structure of claim 7, wherein the functional groups are ion-exchange groups, and wherein the ligands are affinity ligands.

9. The porous self-supporting structure of claim 8, wherein the affinity ligands are proteins.

10. The porous self-supporting structure of claim 1, wherein the inner lumen (20) of component A is a sample collector.

11. An article comprising the porous self-supporting structure according to claim 1 fully contained in a cylindrical housing.

12. The article according to claim 11, wherein the article is a chromatographic unit (30) column or cartridge or a bioconversion reactor or matrix for peptide or oligonucleotides synthesis.

13. The article of claim 12 comprising housing (36) in which the porous self-supporting structure is arranged, the housing (36) having at least one inlet (41) and at east one outlet (40), an inner surface (42) and an outer surface (43), and channel like structure (72) forming a sample distributor (23) on the inner surface (42).

14. The article of claim 13, wherein the channel like structure (72) is a helical groove (25) starting at the area of and being in direct contact with the inlet (41), terminating after at least one complete turn, and not being in direct contact with the outlet (40).

15. The article of claim 14, wherein the chromatographic unit (30) further comprises a first end-fitting (32) and a second end-fitting (38), having O-rings (33 34,35,37) and tightening nuts (31,39).

16. The article of claim 15, wherein the second end-fitting (38) has a top part (52), a bottom part (53) and a casing the second end-fitting (38) is essentially of cylindrical shape, the second end-fitting (38) comprises a collar (5) dividing the cylindrically shaped end-fitting (38) into two parts, whereby the part of the end-fitting (38) nearest to the collar (51) is the top part (52) comprising a connector (50) in connection with a dead-end central bore (54) communicating with a bore (55) which is perpendicular to the dead-end central 1 bore (54), the bore (55) starts in a ring-like groove (56) at the surface of the casing of the second end-fitting (38) and leads into the dead end central bore (54).

17. The article of claim 15, wherein the first end-fitting (32) has a top part (62), a bottom part (63) and a casing, the first end-fitting (32) is essentially of cylindrical shape, the first end-fitting (32) comprises a collar (61) dividing the cylindrically shaped end-fitting (32) into two parts (62,63), whereby the part of the end-fitting (32) nearest to the collar (61) is the bottom part (62) comprising a connector (60) in connection with a central bore (6) extending through the entire first end-fitting (32) and an O-ring (35) placed in a ring-like groove in the casing at the area of the top part (63) of the first end-fitting (32) and O-rings in circular grooves in the top part (63) of the first end-fitting (32).

18. The article of claim 13, wherein the channel like structure (72) is a helical groove (25).

19. The article of claim 13, wherein the chromatographic unit (30) further comprises a first end-fitting (32) or a second end-fitting (38), having O-rings (33,34,35,37) and tightening nuts (31,39).

20. The article of claim 11 further comprising a collecting element (80) disposed in lumen (20), component A, component B, and collecting element (80) forming a concentric assembly.

21. Process for manufacturing a porous self supporting structure of claim 1 comprising the steps of mixing monovinyl and polyvinyl monomers together with porogens and optionally with polymerisation initiators, optionally deaeration, pouring the mixture in a mould for casting a tube-like structure, controlling the temperature in a range of from 40° C. to 90° C., after formation of the polymer removing any porogens, unreacted monomer and initiators, and by-products in a manner to produce the porous self supporting structure of claim 1.

* * * * *